(12) United States Patent
Lindberg

(10) Patent No.: US 7,782,447 B2
(45) Date of Patent: Aug. 24, 2010

(54) ENUMERATION OF THROMBOCYTES

(75) Inventor: Stellan Lindberg, Förslöv (SE)

(73) Assignee: HemoCue AB, Ängelholm (SE)

( * ) Notice: Subject to any disclaimer, the term of this patent is extended or adjusted under 35 U.S.C. 154(b) by 136 days.

(21) Appl. No.: 12/227,870

(22) PCT Filed: Jul. 4, 2007

(86) PCT No.: PCT/SE2007/000655

§ 371 (c)(1),
(2), (4) Date: Dec. 1, 2008

(87) PCT Pub. No.: WO2008/010760

PCT Pub. Date: Jan. 24, 2008

(65) Prior Publication Data

US 2009/0153836 A1    Jun. 18, 2009

(30) Foreign Application Priority Data

Jul. 17, 2006    (SE) .................................... 0601563

(51) Int. Cl.
*G01N 33/48* (2006.01)
(52) U.S. Cl. .......................................... 356/39; 356/36
(58) Field of Classification Search .................... 356/36, 356/39
See application file for complete search history.

(56) References Cited

U.S. PATENT DOCUMENTS

| | | | |
|---|---|---|---|
| 4,240,029 A | 12/1980 | Haynes | |
| 4,978,503 A * | 12/1990 | Shanks et al. | ................ 422/58 |
| 5,674,457 A | 10/1997 | Williamsson et al. | |
| 5,817,519 A | 10/1998 | Zelmanovic et al. | |
| 5,866,349 A | 2/1999 | Lilja et al. | |
| 6,027,904 A | 2/2000 | Devine et al. | |
| 7,068,365 B2 | 6/2006 | Hansen et al. | |

(Continued)

FOREIGN PATENT DOCUMENTS

EP    0549414    6/1993

(Continued)

OTHER PUBLICATIONS

Donat-O. Häder: "Novel Method to Determine Vertical Distributions of Phytoplankton in Marine Water Columns", Enviornmental and Experimental Botany, 1995, pp. 547-555, vol. 35, No. 4, Pergamon.

*Primary Examiner*—Roy Punnoose
(74) *Attorney, Agent, or Firm*—Buchanan Ingersoll & Rooney PC

(57) ABSTRACT

A sample acquiring device for volumetric enumeration of thrombocytes in a blood sample is provided which comprises a measurement cavity for receiving a blood sample. The measurement cavity has a predetermined fixed thickness. The sample acquiring device further comprises a reagent, which is arranged in a dried form on a surface defining the measurement cavity. The reagent comprises a haemolyzing agent for lysing red blood cells in the blood sample, and optionally a staining agent for selectively staining thrombocytes in the blood sample. A system comprises the sample acquiring device and a measurement apparatus. The measurement apparatus comprises a sample acquiring device holder, a light source, and an imaging system for acquiring a digital image of a magnification of the sample. The measurement apparatus further comprises an image analyzer arranged to analyze the acquired digital image for determining the number of thrombocytes in the blood sample.

30 Claims, 2 Drawing Sheets

U.S. PATENT DOCUMENTS 7,521,243 B2 * 4/2009 Lindberg et al. .............. 436/10

FOREIGN PATENT DOCUMENTS

| JP | 2002-148261 A | 5/2002 |
| WO | WO99/45386 A1 | 9/1999 |
| WO | WO 00/25140 | 5/2000 |
| WO | WO03/069421 A2 | 8/2003 |
| WO | WO2005/080940 A1 | 9/2005 |
| WO | WO2006/042555 A2 | 4/2006 |

* cited by examiner

ENUMERATION OF THROMBOCYTES

TECHNICAL FIELD

The present invention relates to a sample acquiring device, a method and a system for volumetric enumeration of thrombocytes in a blood sample.

BACKGROUND OF THE INVENTION

Thrombocytes, or platelets, are circulating blood elements derived from the cytoplasm of a giant cell, the megakaryocyte. They are not strictly cells and do not possess a nucleus. They have important roles in haemostasis, clot retraction, repair of damaged blood vessels and inflammation, and they are generally present in a concentration of about $250 \times 10^9$ per liter blood. The survival time in blood is usually 8-10 days. They are small and disc-shaped with a diameter of about 2 µm and a volume of about 7 fl. A thrombocyte contains substances involved in blood clotting, which substances are stored in certain granules within the thrombocyte and are released upon activation of the thrombocyte, such as at a rift in a blood vessel.

Determining a thrombocyte count is often important in connection with treating a patient. This analysis may be needed for diagnosing a number of disorders. For example, a low thrombocyte count (less than $50 \times 10^9$ per liter blood) is indicative of thrombocytopenia which is a common reason for a predisposition for bleeding. Low thrombocyte concentrations may be due to reduced production, caused by e.g. damaged bone marrow as a result of aplastic anaemia, acute leukaemia, myeloma or cytostatica, reduced survival time of the thrombocytes or a change in the thrombocyte distribution, such as thrombocyte aggregation. On the other hand, an increased thrombocyte concentration may be a result of chronic inflammatory disorders (thrombocytose), such as rheumatic arthritis, or of independent production of thrombocytes in the bone marrow (thrombocytemia) and may lead to blood cloths, thrombosis.

It is desirable to enable analysis results to be obtained as quickly as possible in order to minimize waiting times for patients and enabling a physician to make a decision of treatment and diagnosis directly when making a first examination of the patient. It would therefore be preferable to provide an analysis method which may be quickly performed by the physician or a nurse without the need of sending a test away to a laboratory.

Today, a thrombocyte count is normally obtained with an automated Coulter counter, whereby the blood components (cells and thrombocytes) are identified by means of electrical conductance, or impedance. U.S. Pat. No. 4,240,029 discloses an apparatus for counting platelets and red blood cells by means of an aperture type transducer which is able to size discriminate between the platelets and the red blood cells.

Another automated method for counting platelets uses laser light scatter in a flow cytometer. The platelets are identified by their relatively small size as indicated by the measured light scatter. For instance U.S. Pat. No. 5,817,519 discloses an application of this method.

Other current ways of assessing platelet count are by utilising platelet specific anti bodies, such as disclosed in WO 00/25140, or by measuring the amount of released platelet granule protein, e.g. thrombospondin or β-thromboglobulin, in a sample, such as disclosed in U.S. Pat. No. 6,027,904.

Thrombocytes are also sometimes counted in a microscope in accordance with the Brecher-Cronkite method, whereby a blood sample is mixed with an ammonium oxalate solution after which the thrombocytes, which are visible as light dots with a dark rim, are counted in a phase-contrast microscope. Another known way of counting thrombocytes is by using the commercially available reagent Plaxan™ in combination with a counting chamber, such as a Bürker chamber. A counting chamber is provided with a grid dividing the chamber in well-defined small volumes. The thrombocyte count can then be determined by counting the number of thrombocytes per box in the grid. The thrombocyte count is obtained manually by an analyst, who needs to be experienced in performing the analysis in order to be able to perform a reliable analysis. These analysis are time-consuming. Further, since they are performed manually, the results of the analysis may vary depending on the person performing the analysis.

There is still a need to speed up and simplify existing automated methods for determining a thrombocyte count such that analysis may be provided at point of care.

SUMMARY OF THE INVENTION

It is an object of the invention to provide a simple analysis for determining a volumetric enumeration of thrombocytes. It is a further object of the invention to provide a quick analysis without the need for complicated apparatuses or extensive sample preparations.

These objects are partly or wholly achieved by a sample acquiring device, a method and a system according to the independent claims. Preferred embodiments are evident from the dependent claims.

Thus, there is provided a sample acquiring device for volumetric enumeration of thrombocytes in a blood sample. The sample acquiring device comprises a measurement cavity for receiving a blood sample. The measurement cavity has a predetermined fixed thickness. The sample acquiring device further comprises a reagent, which is arranged in a dried form on a surface defining the measurement cavity, said reagent comprising a haemolysing agent for lysing red blood cells in the blood sample, and, optionally, a staining agent for selectively staining thrombocytes in the blood sample.

The sample acquiring device provides a possibility to directly obtain a sample of whole blood into the measurement cavity and provide it for analysis. There is no need for sample preparation. In fact, the blood sample may be sucked into the measurement cavity directly from a pricked finger of a patient. Providing the sample acquiring device with a reagent enables a reaction within the sample acquiring device which makes the sample ready for analysis. The reaction is initiated when the blood sample comes into contact with the reagent. Thus, there is no need for manually preparing the sample, which makes the analysis especially suitable to be performed directly in an examination room while the patient is waiting.

Since the reagent is provided in a dried form, the sample acquiring device may be transported and stored for a long time without affecting the usability of the sample acquiring device. Thus, the sample acquiring device with the reagent may be manufactured and prepared long before making the analysis of a blood sample.

Whereas many existing methods are able to count different blood cells and even subgroups of blood cells, the sample acquiring device according to the invention is specifically adapted to performing volumetric enumeration of thrombocytes. The reagent comprises a haemolysing agent which will lyse the red blood cells in the blood sample, but not the thrombocytes. This destroys the possibilities to enumerate the red blood cells in the sample. On the other hand, the lysing of the red blood cells simplifies the distinguishing and identification of the thrombocytes within the blood sample. Some intact white blood cells may also be present, but they will be few compared to the thrombocytes and will be easily distinguishable by size and appearance from the thrombocytes.

The optional staining agent provides a marking of the individual thrombocytes. This is one way of enabling the thrombocytes to be individually viewed or detected. Another way of enabling the thrombocytes to be individually viewed or detected is by utilizing a phase contrast approach, preferably with a phase contrast microscope. It is also possible to use a staining agent in combination with a phase contrast approach. The thrombocytes may e.g. be detected by scanning the measurement cavity or obtaining an image of the measurement cavity. The thrombocyte count may thus be obtained by summing the number of individually detected thrombocytes in a defined volume.

The invention also provides a method for volumetric enumeration of thrombocytes in a blood sample. The method comprises acquiring a blood sample into a measurement cavity of a sample acquiring device, said measurement cavity holding a reagent comprising a haemolysing agent, and optionally a staining agent to react with the sample such that the thrombocytes are stained, irradiating the sample with the thrombocytes, acquiring a digital image of a magnification of the irradiated sample in the measurement cavity, wherein thrombocytes are distinguished by selective staining of the staining agent and/or by phase contrast, and digitally analysing the digital image for identifying thrombocytes and determining the number of thrombocytes in the sample.

The invention further provides a system for volumetric enumeration of thrombocytes in a blood sample. The system comprises a sample acquiring device as described above. The system further comprises a measurement apparatus comprising a sample acquiring device holder arranged to receive the sample acquiring device which holds a blood sample in the measurement cavity, and a light source arranged to irradiate the blood sample. The measurement apparatus further comprises an imaging system, comprising a magnifying system and a digital image acquiring means for acquiring a digital image of a magnification of the irradiated sample in the measurement cavity, wherein thrombocytes are distinguished in the digital image by selective staining of the staining agent and/or by phase contrast. The measurement apparatus also comprises an image analyser arranged to analyse the acquired digital image for identifying thrombocytes and determining the number of thrombocytes in the blood sample.

The method and system of the invention provide a very simple analysis of a blood sample for determining a thrombocyte count. The analysis does not require complicated measurement apparatus or advanced steps to be performed by an operator. Therefore, it may be performed in direct connection to examination of a patient, without the need for a qualified technician. The measurement apparatus utilizes the properties of the sample acquiring device for making an analysis on a sample of undiluted whole blood that has been directly acquired into the measurement cavity. The measurement apparatus is arranged to image a volume of the sample for making a volumetric enumeration of the thrombocytes from the one image.

The blood sample is allowed to be mixed with the reagent in the measurement cavity. Within a few minutes, the reaction of the blood sample with the reagent will have haemolysed the red blood cells, and, if a staining agent is provided, stained the thrombocytes, such that the sample is ready for being presented to the optical measurement. The blood sample may be mixed with the reagent by e.g. dispersion or diffusion of the reagent into the blood sample or by actively vibrating or moving the sample acquiring device so that an agitation is caused in the measurement cavity.

The sample acquiring device may comprise a body member having two planar surfaces to define said measurement cavity. The planar surfaces may be arranged at a predetermined distance from one another to determine a sample thickness for an optical measurement. This implies that the sample acquiring device provides a well-defined thickness to the optical measurement, which may be used for accurately determining the thrombocyte count per volumetric unit of the blood sample. A volume of an analysed sample will be well-defined by the thickness of the measurement cavity and an area of the sample being imaged. Thus, the well-defined volume could be used for associating the number of thrombocytes to the volume of the blood sample such that the volumetric thrombocyte count is determined.

The measurement cavity preferably has a uniform thickness of 50-170 micrometers. A thickness of at least 50 micrometers implies that the measurement cavity does not force the blood sample to be smeared into a monolayer allowing a larger volume of blood to be analysed over a small cross-sectional area. Thus, a sufficiently large volume of the blood sample in order to give reliable values of the thrombocyte count may be analysed using a relatively small image of the blood sample. The thickness is more preferably at least 80 micrometers, which allows an even smaller cross-sectional area to be analysed or a larger sample volume to be analysed. Further, the thickness of at least 50 micrometers and more preferably 80 micrometers also simplifies manufacture of the measurement cavity having a well-defined thickness between two planar surfaces.

For most samples arranged in a cavity having a thickness of about 100 micrometers, the thrombocyte count will still be so high that there will be deviations due to thrombocytes being arranged on top of each other. However, the effect of such deviations will be related to the thrombocyte count and may thus be handled by means of statistically correcting results at least for large values of the thrombocyte count. This statistical correction may be based on calibrations of the measurement apparatus. If the cavity thickness is reduced further, to e.g. 50 µm, this correction may be less complex, but this may be balanced against the adverse effects of a low thickness discussed above.

Further, the thickness of the measurement cavity is sufficiently small to enable the measurement apparatus to obtain a digital image such that the entire depth of the measurement cavity may be analysed simultaneously. Since a magnifying system is to be used in the measurement apparatus, it is not simple to obtain a large depth of field. Therefore, the thickness of the measurement cavity would preferably not exceed 150 micrometers in order for the entire thickness to be simultaneously analysed in a digital image. The depth of field may be arranged to handle a thickness of the measurement cavity of 170 micrometers.

The digital image may be acquired with a depth of field at least corresponding to the thickness of the measurement cavity. As used in this context, "depth of field" implies a length in a direction along the optical axis that is imaged in a sufficient focus to allow image analysis to identify cells positioned within this length. This "depth of field" may be larger than a conventional depth of field defined by the optical settings.

Since the digital image is acquired with a "depth of field" at least corresponding to the thickness of the measurement cavity, a sufficient focus is obtained of the entire sample thickness such that the entire thickness of the measurement cavity may be simultaneously analysed in the digital image of the sample. By choosing not to focus very sharply on a specific part of the sample, a sufficient focus is obtained of the entire sample thickness to allow identifying the number of thrombocytes in the sample. This implies that a thrombocyte may be somewhat blurred and still be considered to be in focus of the depth of field.

The reagent, comprising a haemolysing agent, and optionally a staining agent, may be introduced into the measurement cavity of the sample acquiring device dissolved or suspended in a liquid. The reagent may then be turned into a dried form by evaporation at room temperature and pressure, or aided by heat or vacuum, or by lyophilizing. If the reagent is to be evaporated at room temperature and pressure or by heat, the reagent is preferably dissolved or suspended in a volatile liquid, such as methanol.

The reagent, including all its components, of the present invention is preferably dissolvable and/or suspendable in the liquid sample to be analysed, and is preferably intended to stay in solution/suspension throughout the analysis. Since, as stated above, the method is arranged to detect thrombocytes in the entire thickness of the measurement cavity and there is no need to draw or immobilise the thrombocytes to an observation surface, there is also no need to immobilise, or in any other way avoid dissolution/suspension, of the reagent or any component of the reagent. On the contrary, using a dissolvable/suspendable reagent, preferably an easily dissolvable/suspendable reagent, facilitates mixing of the reagent with the liquid sample and accelerates any reactions between the reagent and the liquid sample including the thrombocytes to be measured.

The optional staining agent may be arranged to selectively stain the membrane, the cytoplasm, the granules, or any other part, of the thrombocytes, or a combination thereof. This implies that the thrombocytes may be identified as coloured dots and therefore easily be counted in a digital image.

The optional staining agent may be any one in the group of methylene blue, eosin methylene blue, azure eosin methylene blue, Plaxan™, hematoxylin, methylene green, toluidine blue, gentian violet, sudan analogues, gallocyanine, and fuchsin analogues. However, it should be appreciated that the staining agent is not limited to this group, but many other substances may be contemplated. Preferably the optional staining agent is eosin methylene blue or azure eosin methylene blue The haemolysing agent may be a quaternary ammonium salt, a saponin, a bile acid, such as deoxycholate, a digitoxin, a snake venom, a glucopyranoside or a non-ionic detergent of type Triton. However, it should be appreciated that the haemolysing agent is not limited to this group, but many other substances may be contemplated. Preferably the haemolysing agent is a saponin.

The sample acquiring device may further comprise a sample inlet communicating the measurement cavity with the exterior of the sample acquiring device, said inlet being arranged to acquire a blood sample. The sample inlet may be arranged to draw up a blood sample by a capillary force and the measurement cavity may further draw blood from the inlet into the cavity. As a result, the blood sample may easily be acquired into the measurement cavity by simply moving the sample inlet into contact with blood. Then, the capillary forces of the sample inlet and the measurement cavity will draw up a well-defined amount of blood into the measurement cavity. Alternatively, the blood sample may be sucked or pushed into the measurement cavity by means of applying an external pumping force to the sample acquiring device. According to another alternative, the blood sample may be acquired into a pipette and then be introduced into the measurement cavity by means of the pipette.

The sample acquiring device may be disposable, i.e. it is arranged to be used once only. The sample acquiring device provides a kit for performing a thrombocyte count, since the sample acquiring device is able to receive a blood sample and holds all reagents needed in order to present the sample to cell counting. This is particularly enabled since the sample acquiring device is adapted for use once only and may be formed without consideration of possibilities to clean the sample acquiring device and re-apply a reagent. Also, the sample acquiring device may be moulded in plastic material and thereby be manufactured at a low price rate. Thus, it may still be cost-effective to use a disposable sample acquiring device.

If a staining agent is used, the sample may be irradiated by light of a wavelength corresponding to a peak in absorbance of the staining agent. Consequently, the stained thrombocytes which contain an accumulation of staining agent will be detected by a low transmittance of light.

In this case, the irradiating may be performed by means of a laser source. The laser source may provide light of a well-defined wavelength fitting the absorbance of the staining agent. Further, the laser source provides collimated light, minimizing disturbances of stray light, such that a point of low transmittance of light will be sharply distinguished.

The irradiating may alternatively be performed by means of a light emitting diode. This light source may still provide sufficient irradiating conditions for properly distinguishing thrombocytes from other matter in the sample.

Alternatively, especially if phase contrast is utilized, a tungsten-halogen lamp may be used to irradiate the sample.

The digital image may be acquired using a magnification power of 3-200×, more preferably 4-20×. Within these ranges of magnification power, the thrombocytes are sufficiently magnified in order to be detected, while the depth of field may be arranged to cover the sample thickness. A low magnification power implies that a large depth of field may be obtained. However, if a low magnification power is used, the thrombocytes may be hard to detect. A lower magnification power may be used by increasing the number of pixels in the acquired image, that is by improving the resolution of the digital image.

One alternative is to use a phase contrast microscope, utilising the phase shift resulting from some of the light illuminating a blood sample encountering membranes and other structures, etc. In this case the thrombocytes of the blood sample analysed will appear as light, glittering dots with a dark periphery.

The analysing comprises identifying areas of high light absorbance in the digital image. The analysing may further comprise identifying black or dark dots in the digital image, or, when phase contrast is used (with high enough magnification), dark rings corresponding to the thrombocyte periphery.

The analysing may further comprise electronically magnifying the acquired digital image. While the sample is being magnified for acquiring a magnified digital image of the sample, the acquired digital image itself may be electronically magnified for simplifying distinguishing between objects that are imaged very closely to each other in the acquired digital image.

BRIEF DESCRIPTION OF THE DRAWINGS

The invention will now be described in further detail by way of example under reference to the accompanying drawings.

DETAILED DESCRIPTION OF A PREFERRED EMBODIMENT

Figure 1:
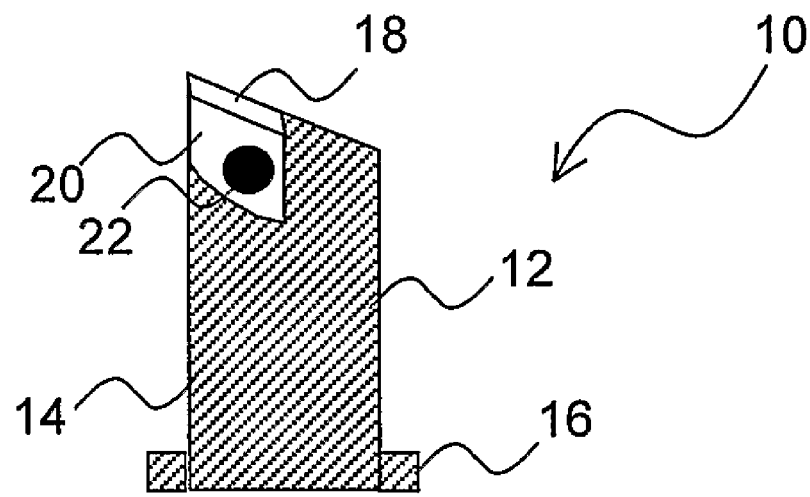
FIG. 1 is a schematic view of a sample acquiring device according to an embodiment of the invention.

Referring now to FIG. 1, a sample acquiring device 10 according to an embodiment of the invention will be described. The sample acquiring device 10 is disposable and is to be thrown away after having been used for analysis. This implies that the sample acquiring device 10 does not require complicated handling. The sample acquiring device 10 is preferably formed in a plastic material and may be manufactured by injection-moulding. This makes manufacture of the sample acquiring device 10 simple and cheap, whereby the costs of the sample acquiring device 10 may be kept down.

The sample acquiring device 10 comprises a body member 12, which has a base 14, which may be touched by an operator without causing any interference in analysis results. The base 14 may also have projections 16 that may fit a holder in an analysis apparatus. The projections 16 may be arranged such that the sample acquiring device 10 will be correctly positioned in the analysis apparatus.

The sample acquiring device 10 further comprises a sample inlet 18. The sample inlet 18 is defined between opposite walls within the sample acquiring device 10, the walls being arranged so close to each other that a capillary force may be created in the sample inlet 18. The sample inlet 18 communicates with the exterior of the sample acquiring device 10 for allowing blood to be drawn into the sample acquiring device 10. The sample acquiring device 10 further comprises a measurement cavity 20 arranged between opposite walls inside the sample acquiring device 10. The measurement cavity 20 is arranged in communication with the sample inlet 18. The walls defining the measurement cavity 20 are arranged closer together than the walls of the sample inlet 18, such that a capillary force may draw blood from the sample inlet 18 into the measurement cavity 20.

The walls of the measurement cavity 20 are arranged at a distance from each other of 50-170 micrometers, and more preferably 80-150 micrometers. The distance is uniform over the entire measurement cavity 20. The thickness of the measurement cavity 20 defines the volume of blood being examined. Since the analysis result is to be compared to the volume of the blood sample being examined, the thickness of the measurement cavity 20 needs to be very accurate, i.e. only very small variations in the thickness are allowed within the measurement cavity 20 and between measurement cavities 20 of different sample acquiring devices 10. The thickness allows a relatively large sample volume to be analysed in a small area of the cavity. The thickness theoretically allows thrombocytes to be arranged on top of each other within the measurement cavity 20, but this may be accounted for with a statistical model.

A surface of a wall of the measurement cavity 20 is at least partly coated with a reagent 22. The reagent 22 may be freeze-dried, heat-dried or vacuum-dried and applied to the surface of the measurement cavity 20. When a blood sample is acquired into the measurement cavity 20, the blood will make contact with the dried reagent 22 and initiate a reaction between the reagent 22 and the blood.

The reagent 22 is applied by inserting the reagent 22 into the measurement cavity 20 using a pipette or dispenser. The reagent 22 is solved in water or an organic solvent when inserted into the measurement cavity 20. The solvent with the reagent 22 may fill the measurement cavity 20. Then, drying is performed such that the solvent will be evaporated and the reagent 22 will be attached to the surfaces of the measurement cavity 20.

According to an alternative manufacturing method, the sample acquiring device 10 may be formed by attaching two pieces to each other, whereby one piece forms the bottom wall of the measurement cavity 20 and the other piece forms the top wall of the measurement cavity 20. This allows a reagent 22 to be dried onto an open surface before the two pieces are attached to each other.

The reagent 22 comprises a haemolysing agent, and optionally a staining agent. The haemolysing agent may be a quaternary ammonium salt, a saponin, a bile acid, such as deoxycholate, a digitoxin, a snake venom, a glucopyranoside or a non-ionic detergent of type Triton, preferably a saponin. The staining agent, if used, may be methylene blue, eosin methylene blue, azure eosin methylene blue, Plaxan™, hematoxylin, methylene green, toluidine blue, gentian violet, a sudan analogue, gallocyanine, or a fuchsin analogue. When a blood sample makes contact with the reagent 22, the haemolysing agent will act to lyse the red blood cells such that the red blood cells are mixed with the blood plasma. Further, the staining agent, if used, may accumulate in the thrombocytes, e.g. in the membranes thereof. If a staining agent is used, the reagent 22 should contain sufficient amounts of staining agent to distinctly stain all of the thrombocytes. Thus, there will often be a surplus of staining agent, which will be intermixed in the blood plasma. The surplus of staining agent will give a homogenous, low background level of staining agent in the blood plasma. The accumulated staining agent in the thrombocytes will be distinguishable over the background level of staining agent.

The reagent 22 may also comprise other constituents, which may be active, i.e. taking part in the chemical reaction with the blood sample, or non-active, i.e. not taking part in the chemical reaction with the blood sample. The active constituents may e.g. be arranged to catalyse the haemolysing or staining action. The non-active constituents may e.g. be arranged to improve attachment of the reagent 22 to the surface of a wall of the measurement cavity 20.

Within a few minutes, the blood sample will have reacted with the reagent 22, such that the red blood cells have been lysed and the staining agent, if used, has accumulated in the thrombocytes.

Figure 2:
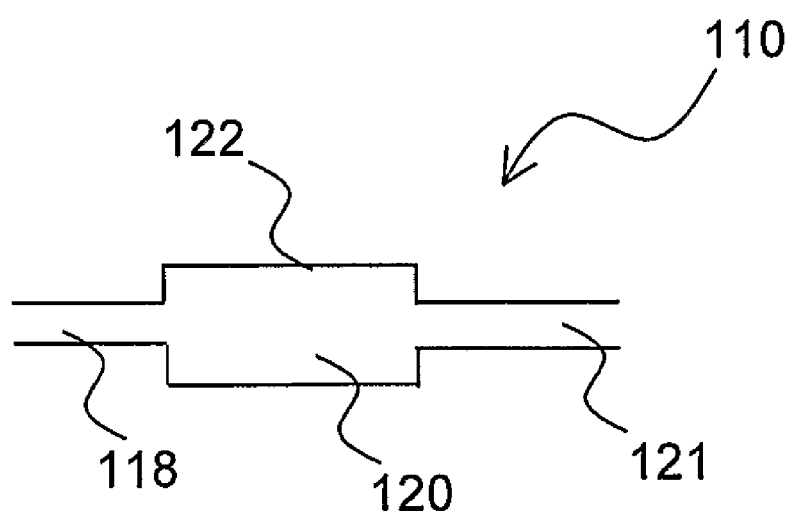
FIG. 2 is a schematic view of a sample acquiring device according to another embodiment of the invention.

Referring to FIG. 2, another embodiment of the sample acquiring device will be described. The sample acquiring device 110 comprises a chamber 120 forming the measurement cavity. The sample acquiring device 110 has an inlet 118 into the chamber 120 for transporting blood into the chamber 120. The chamber 120 is connected to a pump (not shown) via a suction tube 121. The pump may apply a suction force in the chamber 120 via the suction tube 121 such that blood may be sucked into the chamber 120 through the inlet 118. The sample acquiring device 110 may be disconnected from the pump before measurement is performed. Like the measurement cavity of the sample acquiring device, the chamber 120 has a well-defined thickness defining the thickness of the sample to be examined. Further, a reagent 122 is applied to walls of the chamber 120 for reacting with the blood sample.

Figure 3:
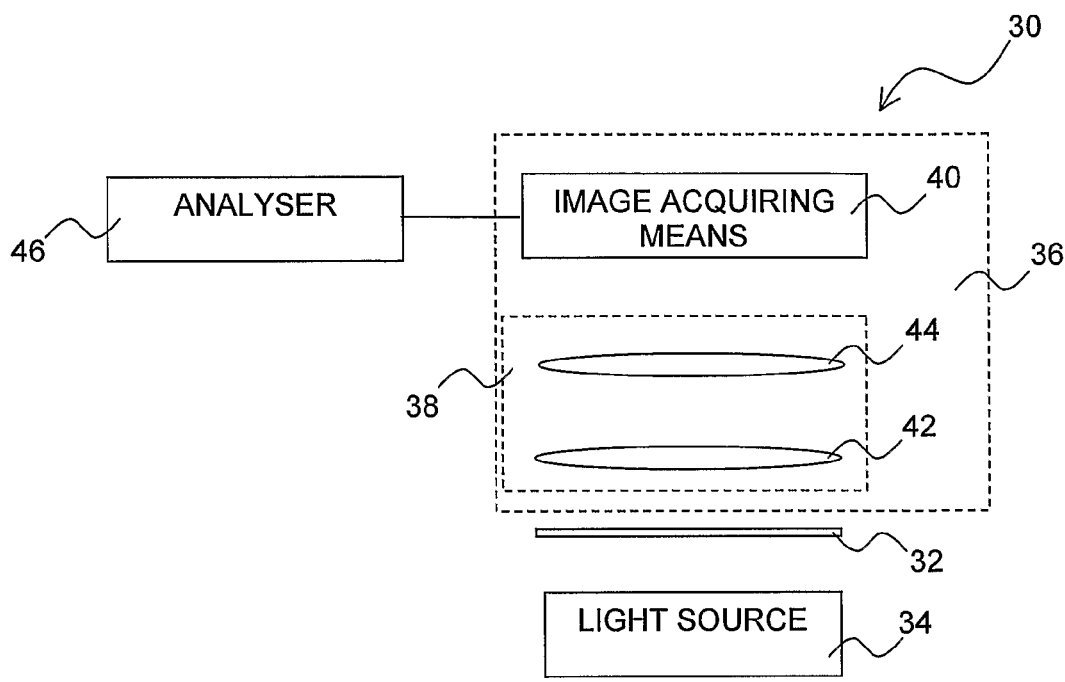
FIG. 3 is a schematic view of a measurement apparatus according to an embodiment of the invention.

Referring now to FIG. 3, an apparatus 30 for volumetric enumeration of thrombocytes will be described. The apparatus 30 comprises a sample holder 32 for receiving a sample acquiring device 10 with a blood sample. The sample holder 32 is arranged to receive the sample acquiring device 10 such that the measurement cavity 20 of the sample acquiring device 10 is correctly positioned within the apparatus 30. The apparatus 30 comprises a light source 34 for illuminating the blood sample within the sample acquiring device 10. The light source 34 may be an incandescent lamp, which irradiates light in the entire visible spectrum.

If a staining agent is used, the staining agent accumulated in the thrombocytes will absorb light of specific wavelengths, such that the thrombocytes will emerge in a digital image of the sample. If a colour image is acquired, the thrombocytes will emerge as specifically coloured dots. If a black and white image is acquired, the thrombocytes will emerge as dark dots against a lighter background.

If a phase contrast approach is utilized, no staining is needed, although it may be practical to stain anyway in order to further facilitate the detection of the thrombocytes, and the thrombocytes will emerge as light dots with dark circumference.

The light source 34 may alternatively be a laser or a light emitting diode. This may be used for increasing contrast in the image such that the thrombocytes may be more easily detected. In this case, the light source 34 is arranged to radiate electromagnetic radiation of a wavelength that corresponds to an absorption peak of the staining agent. The wavelength should further be chosen such that the absorption of the blood compounds is relatively low. Further, the sample acquiring device walls should be essentially transparent to the wavelength. For example, if methylene blue is used as a staining agent, the light source 34 may be arranged to irradiate light having a wavelength of 667 nm.

The apparatus 30 further comprises an imaging system 36, which is arranged on an opposite side of the sample holder 32 relative to the light source 34. Thus, the imaging system 36 is arranged to receive radiation which has been transmitted through the blood sample. The imaging system 36 comprises a magnifying system 38 and an image acquiring means 40. The magnifying system 38 is arranged to provide a magnifying power of 3-200×, more preferably 4-20×. Within these ranges of magnifying power, it is possible to distinguish the thrombocytes. Further, the depth of field of the magnifying system 38 may still be arranged to at least correspond to the thickness of the measurement cavity 20.

The magnifying system 38 comprises an objective lens or lens system 42, which is arranged close to the sample holder 32, and an ocular lens or lens system 44, which is arranged at a distance from the objective lens 42. The objective lens 42 provides a first magnification of the sample, which is further magnified by the ocular lens 44. The magnifying system 38 may comprise further lenses for accomplishing an appropriate magnification and imaging of the sample. The magnifying system 38 is arranged such that the sample in the measurement cavity 20 when placed in the sample holder 32 will be focussed onto an image plane of the image acquiring means 40.

If a phase contrast microscope is comprised in the measurement apparatus of FIG. 3, a condenser and a condenser annulus are included between the light source 34 and the sample holder 32, and a phase plate is included between the objective lens 42 and the image acquiring means 40.

The image acquiring means 40 is arranged to acquire a digital image of the sample. The image acquiring means 40 may be any kind of digital camera, such as a CCD-camera. The pixel size of the digital camera sets a restriction on the imaging system 36 such that the circle of confusion in the image plane may not exceed the pixel size within the depth of field. The digital camera 40 will acquire a digital image of the sample in the measurement cavity 20, wherein the entire sample thickness is sufficiently focussed in the digital image for counting the thrombocytes. The imaging system 36 will define an area of the measurement cavity 20, which will be imaged in the digital image. The area being imaged together with the thickness of the measurement cavity 20 defines the volume of the sample being imaged. The imaging system 36 is set up to fit imaging blood samples in sample acquiring devices 10. There is no need to change the setup of the imaging system 36. Preferably, the imaging system 36 is arranged within a housing such that the setup is not accidentally changed.

The apparatus 30 further comprises an image analyser 46. The image analyser 46 is connected to the digital camera 40 for receiving digital images acquired by the digital camera 40. The image analyser 46 is arranged to identify patterns in the digital image that correspond to a thrombocyte for counting the number of thrombocytes being present in the digital image. Thus, the image analyser 46 may be arranged to identify dark dots in a lighter background. The image analyser 46 may be arranged to first electronically magnify the digital image before analysing the digital image. This implies that the image analyser 46 may be able to more easily distinguish thrombocytes that are imaged closely to each other, even though the electronic magnifying of the digital image will make the digital image somewhat blurred.

The image analyser 46 may calculate the number of thrombocytes per volume of blood by dividing the number of thrombocytes being identified in the digital image with the volume of the blood sample, which is well-defined as described above. The volumetric thrombocyte count may be presented on a display of the apparatus 30.

The image analyser 46 may be realised as a processing unit, which comprises codes for performing the image analysis.

Figure 4:
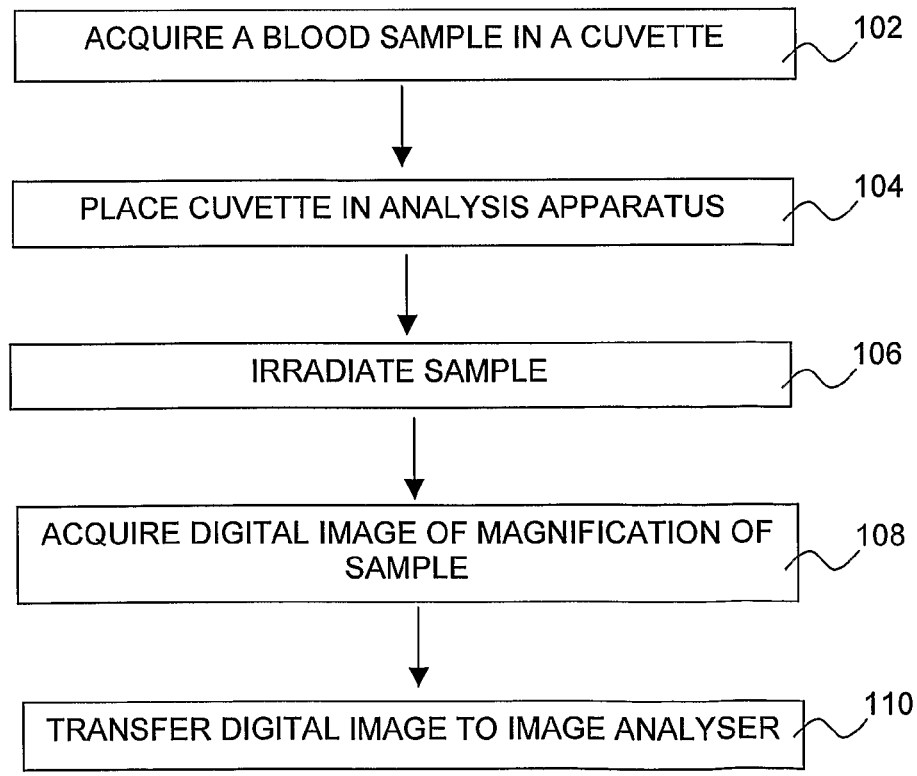
FIG. 4 is a flow chart of a method according to an embodiment of the invention.

Referring to FIG. 4, a method for volumetric enumeration of thrombocytes will be described. The method comprises acquiring a blood sample in a sample acquiring device, step 102. An undiluted sample of whole blood is acquired in the sample acquiring device. The sample may be acquired from capillary blood or venous blood. A sample of capillary blood may be drawn into the measurement cavity directly from a pricked finger of a patient. The blood sample makes contact with a reagent in the sample acquiring device initiating a reaction. The red blood cells will be lysed and a staining agent is accumulated in the thrombocytes. Within a few minutes from acquiring the blood sample, the sample is ready to be analysed. The sample acquiring device is placed in an analysis apparatus, step 104. An analysis may be initiated by pushing a button of the analysis apparatus. Alternatively, the analysis is automatically initiated by the apparatus detecting the presence of the sample acquiring device.

The sample is irradiated, step 106, and a digital image of a magnification of the sample is acquired, step 108. The sample is being irradiated with electromagnetic radiation of a wavelength corresponding to an absorption peak of the staining agent. This implies that the digital image will contain black or darker dots in the positions of the thrombocytes.

The acquired digital image is transferred to an image analyser, which performs image analysis, step 110, in order to count the number of black dots in the digital image.

The method and apparatus presented here may for example be arranged to count approximately 25,000 thrombocytes, which gives better statistical certainty of the obtained results. A normal, healthy adult has a thrombocytes count of about $250 \times 10^9$ thrombocytes/liter blood. This implies that 25,000 thrombocytes are found in samples having a volume of about 0.1 µl. For example, if an area of 1.0×1.0 mm in the measurement cavity having a thickness of 100 µm is imaged, the volume being imaged is 0.10 µl. A part of the acquired image may be selected for analysis. Thus, the acquired image may first be coarsely analysed such that no anomalies are allowed in the part being used for determining the thrombocyte count. The part of the acquired imaged selected for analysis may be selected having an appropriate size so that a sufficient volume of the blood sample will be analysed.

It should be emphasized that the preferred embodiments described herein are in no way limiting and that many alternative embodiments are possible within the scope of protection defined by the appended claims.

The invention claimed is:

1. A sample acquiring device for volumetric enumeration of thrombocytes in a blood sample, said sample acquiring device comprising:
    a measurement cavity for receiving a blood sample, said measurement cavity having a predetermined fixed thickness, and
    a reagent, which is arranged in a dried form on a surface defining the measurement cavity, said reagent comprising a haemolysing agent for lysing red blood cells in the blood sample and said reagent further comprising a staining agent for selectively staining thrombocytes in said blood sample.

2. The sample acquiring device according to claim 1, wherein the sample acquiring device comprises a body member having two planar surfaces to define said measurement cavity.

3. The sample acquiring device according to claim 2, wherein the planar surfaces are arranged at a predetermined distance from one another to determine a sample thickness for an optical measurement.

4. The sample acquiring device according to claim 1, wherein the measurement cavity has a uniform thickness of 50-170 micrometers.

5. The sample acquiring device according to claim 1, wherein the staining agent is arranged to selectively stain the membranes of the thrombocytes.

6. The sample acquiring device according to claim 1, wherein the staining agent is any one in the group of methylene blue, eosin methylene blue, azure eosin methylene blue, Plaxan ™, hematoxylin, methylene green, toluidine blue, gentian violet, a sudan analogue, gallo-cyanine, or a fuchsin analogue.

7. The sample acquiring device according to claim 1, wherein the haemolysing agent is a quaternary ammonium salt, a saponin, a bile acid, a digitoxin, a snake venom, a glucopyranoside, or a non-ionic detergent of type Triton.

8. The sample acquiring device according to claim 1, further comprising a sample inlet communicating the measurement cavity with the exterior of the sample acquiring device, said inlet being arranged to acquire a blood sample.

9. A system for volumetric enumeration of thrombocytes in a blood sample, said system comprising:
    a sample acquiring device according to claim 1, and
    a measurement apparatus comprising:
        a sample acquiring device holder arranged to receive the sample acquiring device which holds a blood sample in the measurement cavity,
        a light source arranged to irradiate the blood sample,
        an imaging system, comprising a magnifying system and a digital image acquiring means for acquiring a digital image of a magnification of the irradiated sample in the measurement cavity, wherein thrombocytes are distinguished in the digital image by selective staining of the staining agent and/or by phase contrast, and
        an image analyser arranged to analyse the acquired digital image for identifying thrombocytes and determining the number of thrombocytes in the blood sample.

10. The system according to claim 9, wherein the magnifying system is arranged with a depth of field of at least the thickness of the measurement cavity of the sample acquiring device.

11. The system according to claim 10, wherein a volume of an analysed sample is well-defined by the thickness of the measurement cavity and an area of the sample being imaged.

12. The system according to claim 9, wherein a volume of an analysed sample is well-defined by the thickness of the measurement cavity and an area of the sample being imaged.

13. The system according to claim 9, wherein the light source is arranged to irradiate light of a wavelength corresponding to a peak in absorbance of the staining agent.

14. The system according to claim 9, wherein said light source comprises a laser source.

15. The system according to claim 9, wherein said light source comprises a light emitting diode.

16. The system according to claim 9, wherein the magnifying system has a magnification power of 3-200×.

17. The system according to claim 9, wherein the image analyser is arranged to identify areas of high light absorbance in the digital image.

18. The system according to claim 17, wherein the image analyser is arranged to identify black dots in the digital image.

19. The system according to claim 9, wherein the image analyser is arranged to electronically magnify the acquired digital image.

20. A method for volumetric enumeration of thrombocytes in a blood sample, said method comprising:
    acquiring a blood sample into a measurement cavity of a sample acquiring device, said measurement cavity holding a reagent comprising a haemolysing agent and optionally a staining agent to react with the sample such that the thrombocytes are stained, the reagent being arranged in a dried form in said measurement cavity,
    irradiating the sample with the thrombocytes,
    acquiring a digital image of a magnification of the irradiated sample in the measurement cavity, wherein thrombocytes are distinguished by selective staining of the staining agent and/or by phase contrast, said digital image being acquired with a depth of field at least corresponding to the thickness of the measurement cavity, and
    digitally analysing the digital image for identifying thrombocytes and determining the number of thrombocytes in the sample.

21. The method according to claim 20, wherein the blood sample is mixed with the reagent in the measurement cavity.

22. The method according to claim 20, wherein the measurement cavity has a thickness of 50-170 micrometers.

23. The method according to claim 22, wherein a volume of an analysed sample is well-defined by the thickness of the measurement cavity and an area of the sample being imaged.

24. The method according to claim 20, wherein the sample is irradiated by light of a wavelength corresponding to a peak in absorbance of the staining agent.

25. The method according to claim 20, wherein said irradiating is performed by means of a laser source.

26. The method according to claim 20, wherein said irradiating is performed by means of a light emitting diode.

27. The method according to claim 20, wherein the digital image is acquired using a magnification power of 3-200×.

28. The method according to claim 20, wherein said analysing comprises identifying areas of high light absorbance in the digital image.

29. The method according to claim 28, wherein said analysing comprises identifying black dots in the digital image.

30. The method according to claim 20, wherein said analysing comprises electronically magnifying the acquired digital image.

* * * * *